US006235732B1

(12) United States Patent
Dollinger et al.

(10) Patent No.: US 6,235,732 B1
(45) Date of Patent: May 22, 2001

(54) NEUROKININ ANTAGONISTS

(75) Inventors: Horst Dollinger, Ingelheim/Rhein; Gerd Schnorrenberg, Gau-Algesheim; Hans Briem, Budenheim; Birgit Jung, Bingen/Rhein; Georg Speck, Ingeheim/Rhein, all of (DE)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/250,342

(22) Filed: Feb. 16, 1999

Related U.S. Application Data

(62) Division of application No. 08/905,251, filed on Aug. 2, 1997, now Pat. No. 5,985,881, which is a division of application No. 08/473,423, filed on Jun. 7, 1995, now Pat. No. 5,696,123.

(30) Foreign Application Priority Data

Sep. 17, 1994 (DE) .................................. 44 33 208
Jun. 3, 1995 (DE) .............................. 195 20 499

(51) Int. Cl.[7] .................... A61K 31/495; A61P 11/06; A61P 19/02; C07D 295/04
(52) U.S. Cl. ................................. 514/227.5; 514/231.5; 544/59; 544/106; 544/111; 546/124
(58) Field of Search ............... 544/59, 106, 111; 514/227.5, 231.5; 546/124; 564/48, 185, 182, 306

(56) References Cited

U.S. PATENT DOCUMENTS

| | | | |
|---|---|---|---|
| 5,696,123 | 12/1997 | Dollinger et al. | 544/392 |
| 5,708,006 | 1/1998 | Dollinger et al. | 546/190 |

FOREIGN PATENT DOCUMENTS

WO 93/10073   5/1993   (WO).
93 22279  *  11/1993   (WO).

OTHER PUBLICATIONS

Nagarajan et al. Proc. Indian Acad. Sci., Chem. Sci. 104(3) 383–97, CA 117:111219, 1992.*
John A. Lowe, III; Nonpeptide Tachykinin Antagonists: Medicinal Chemistry and Molecular Biology, Medicinal Research Reviews, vol. 16, No. 6, 527–545(1996).
S. McLean; Nonpeptide Antagonists of NK1, Tachykinin Receptor: Medicinal Research Reviews, vol. 16, No. 4, 297–317 (1996).
James L. Henry; Substance P and Inflammatory Pain: Potential of Substance P Antagonists as Analgesics, Inflammatory Disease Therapy—Preclinical and Clinical Development, pp. 75–87 (1993).
Saliha M. Moussaoui, et al; Inhibition of neurogenic inflammation in the meninges by a non–peptide NK1 receptor antagonist. RP 67580, European Journal of Pharmacology, 238 (1993) 421–424.

* cited by examiner

Primary Examiner—Richard L. Raymond
Assistant Examiner—Venkataraman Balasubramanian
(74) Attorney, Agent, or Firm—R. P. Raymond; Timothy X. Witkowski; Anthony P. Bottino

(57) ABSTRACT

The invention relates to new compounds of general formula I

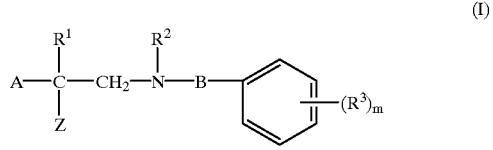

and the pharmaceutically acceptable salts thereof, wherein A, B, Z, $R^1$, $R^2$, $R^3$ and m are defined as in the specification, processes for preparing them and pharmaceutical compositions containing these compounds. The compounds are valuable neurokinin (tachykinin) antagonists.

17 Claims, No Drawings

NEUROKININ ANTAGONISTS

This is a division of application Ser. No. 08/905,251 filed Aug. 2, 1997, now U.S. Pat. No. 5,985,851 which is a division of Ser. No. 08/473,423 now U.S. Pat. No. 5,696,123 filed Jun. 7, 1995.

The invention relates to new compounds of general formula I

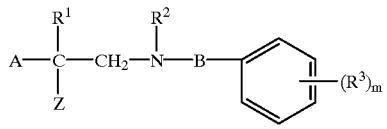

I and the pharmaceutically acceptable salts thereof, processes for preparing them and pharmaceutical compositions containing these compounds. The compounds are valuable neurokinin (tachykinin)-antagonists.

The International Patent Application WO 93/10073 describes compounds having a similar structure and a neurokinin-antagonistic activity. These compounds are specifically excluded from the subject matter of the present application.

The present invention relates to compounds of general formula I

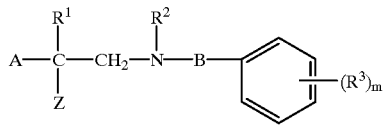

I and the pharmaceutically acceptable salts thereof, wherein

A denotes Ar, Ar—CH$_2$—, Ar—CH(Ph)—, Ar—(CH$_2$)$_2$—, Ar—CH(Ph)—CH$_2$—, Ar—CH$_2$—CH(Ph)— or Ar—CH(Ph)—CH(Ph)—, wherein Ar denotes phenyl, naphthyl, pyridyl or thienyl and Ph denotes phenyl, whilst the phenyl groups contained in these groups may be unsubstituted or substituted by one, two or three R$^4$ groups, wherein these R$^4$ groups independently of one another denote (C$_{1-6}$)alkyl, (C$_{1-6}$)alkyl substituted by 1 to 3 fluorine atoms, (C$_{1-6}$)alkoxy, (C$_{1-6}$)alkylthio or halogen, or two adjacent R$^4$ groups together denote —O—(CH$_2$)—O— or —(CH$_2$)$_{3-5}$—;

B denotes —CH(R$^{12}$)—,
—CH$_2$—CH$_2$—,
—C(O)—NH—,
—C(O)—CH$_2$— or
—C(O)—CH$_2$—CH$_2$—;
wherein
R$^{12}$ denotes H or CH$_3$;

R$^1$ denotes H, (C$_{1-6}$)alkyl or phenyl;

R$^2$ denotes H, (C$_{1-6}$)alkyl or —C(O)(C$_{13}$)alkyl, wherein the alkyl groups contained therein may be substituted by a phenyl group;

R$^3$ denotes hydrogen, (C$_{1-6}$)alkyl, (C$_{1-6}$)alkyl substituted by 1 to 3 fluorine atoms, halogen or (C$_{1-6}$)alkoxy;

m is 1, 2 or 3;
z is di(C$_{1-6}$)alkylamine,

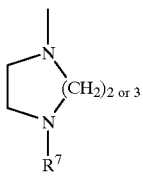

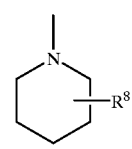

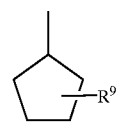

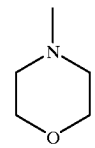

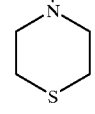

or

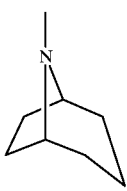

, wherein
R$^7$ denotes hydrogen, (C$_{3-7}$)cycloalkyl, phenyl

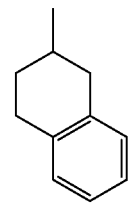

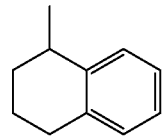

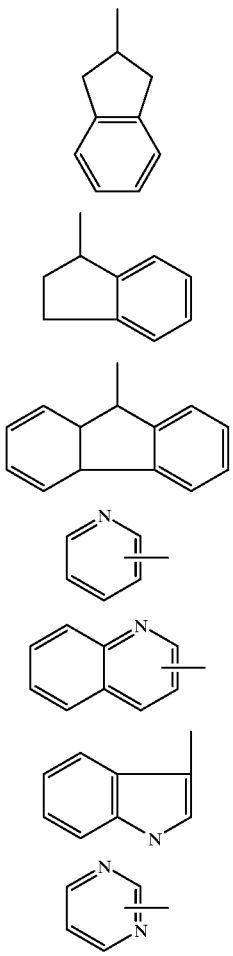

(C₁₋₆)alkyl,
allyl,
—(CH₂)₂₋₆OH,
—(C₁₋₃)alkylphenyl,
diphenylmethyl or
—(C₁₋₃)alkyl(C₃₋₇)cycloalkyl, whilst the phenyl groups contained in the above-mentioned groups may be unsubstituted or substituted by one or two substituents, namely CH₃, F, Cl, OCH₃, SCH₃, CF₃, OH or NO₂, or they may be substituted by —O—CH₂—O— linked to 2 adjacent carbon atoms of the phenyl;

$R^8$ and $R^9$ have the meanings given under the definition of $R^7$ or denote
—CH₂OH
—OH

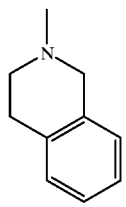

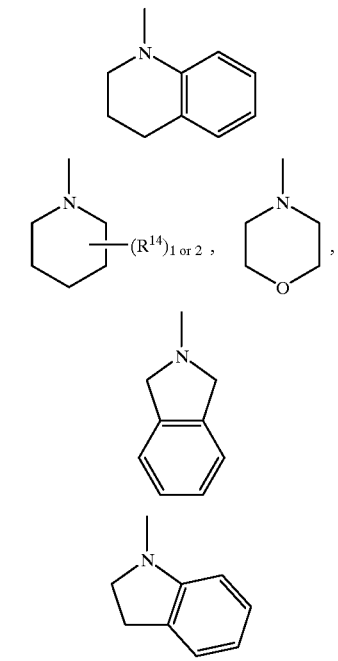

wherein the last six groups mentioned are in position 3 or 4, in the case of $R^8$, and in position 3, in the case of $R^9$, and wherein
$R^{14}$ denotes H,
(C₁–C₆) alkyl,
phenyl or
cyclohexyl,
whilst if one of the $R^{14}$ groups is phenyl or cyclohexyl, the other $R^{14}$ must be hydrogen;

With the exception of compounds of general formula I wherein
A, $R^3$ and m are as herein before defined;
B denotes —CH—₂,
$R^1$ denotes H, alkyl or phenyl,
$R^2$ is H and
z is —N(CH₃)₂,

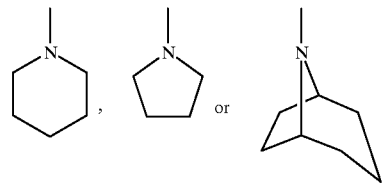

Compounds of general formula I contain basic groups. The ompounds of general formula I can therefore occur in the form of salts with pharmaceutically acceptable inorganic acids such as hydrochloric acid, sulphuric acid, phosphoric acid, sulphonic acid or organic acids (such as, for example, maleic acid, fumaric acid, citric acid, tartaric acid or acetic acid).

The compounds of general formula I may contain chiral centres: the formulae given includes the mixtures of isomers as well as the individual isomers.

The terms "alkyl" and "alkoxy" appearing in the definitions include both branched and unbranched alkyl and alkoxy groups.

Preferred compounds of general formula I are those wherein

A represents Ar, Ar—CH$_2$—, Ar—CH(Ph)—, Ar—(CH$_2$)$_2$—, Ar—CH(Ph)—CH$_2$—, Ar—CH$_2$—CH(Ph)— or Ar—CH(Ph)—CH(Ph)—, wherein Ar denotes phenyl or naphthyl and Ph represents phenyl, whilst the phenyl groups contained in these groups may be unsubsituted or may be substituted by one, two or three R$^4$ groups, wherein these R$^4$ groups independently of one another denote (C$_1$–C$_3$) alkyl, (C$_1$–C$_3$)alkyl substituted by one to three fluorine atoms, (C$_1$–C$_3$) alkoxy, (C$_1$–C$_3$)alkylthio or halogen, or two adjacent R$^4$ groups together denote —O—(CH$_2$)—O—;

B denotes —CH(R$^{12}$)—,
—CH$_2$—CH$_2$—,
C(O)—,
—(O)—NH—,
—C(O)—CH$_2$—or
—C(O)—CH$_2$—CH$_2$—;
wherein
R$^{12}$ denotes H or CH$_3$;

R$^1$ denotes H, (C$_{1-3}$)alkyl or phenyl;

R$^2$ denotes H, (C$_{1-3}$)alkyl or —C(O)(C$_{1-3}$)alkyl, whilst the alkyl groups contained therein may be substituted by a phenyl group;

R$^3$ denotes hydrogen, (C$_{1-3}$)alkyl, (C$_{1-3}$)alkyl substituted by 1 to 3 fluorine atoms, halogen or (C$_{1-3}$)alkoxy;

m is 1, 2 or 3;

and Z is as herein before defined.

Particular mention should be made of compounds of general formula 1 wherein A is phenyl, benyzl, diphenylmethyl or naphthyl, particularly compounds wherein A is unsubstituted phenyl or phenyl substituted by 1 or 2 R$^4$ groups, these R$^4$ groups independently of one another representing methyl, trifluoromethyl, methoxy, thiomethyl, fluorine or chlorine, preferably compounds wherein A is phenyl or methoxyphenyl; and/or B is —CH$_2$—,
—CH—(CH$_3$)—,
—CH$_2$—CH$_2$—,
—C(O)—NH— or
—C(O)—CH$_2$—
and/or R$^1$ is hydrogen; and/or R$^2$ is —C(O)CH$_3$ or hydrogen; and/or R$^3$ is hydrogen, methyl, trifluoromethyl, methoxy, i-propoxy, fluorine or chlorine and/or m is 1 or 2;

particularly wherein m is 2 and are R$^3$ is trifluoromethyl in positions 3 and 5 or wherein m is one and R$^3$ is i-propoxy in position 3; and/or Z denotes

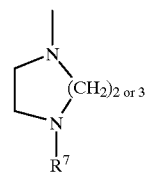

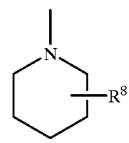

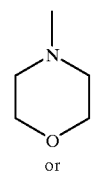

or

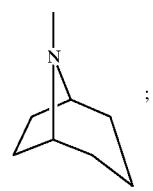

;

wherein R$^7$ denotes (C$_5$–C$_7$)cycloalkyl, phenyl

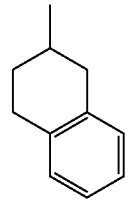

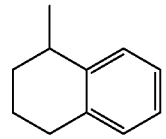

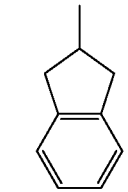

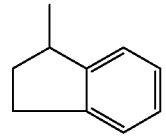

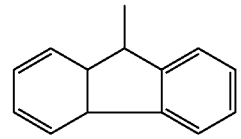

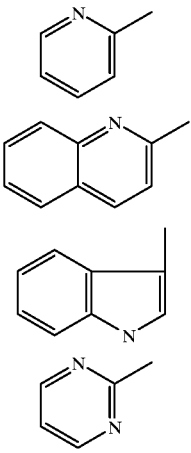

(C₁–C₃)alkyl, allyl,

—(CH₂)₂OH,

—(C1–C₂)alkylphenyl, diphenylmethyl or

—(C₁–C₂)alkylcyclohexyl, wherein the phenyl groups contained in the above-mentioned groups may be unsubstituted or substituted by one or two substituents, namely $CH_3$, F, Cl, $OCH_3$, $SCH_3$, $CF_3$, OH or $NO_2$ or may be substituted by —O—CH₂—O— which is linked to two adjacent carbon atoms of the phenyl, particularly wherein Z is piperazinyl substituted by $R^7$ or wherein Z is homopiperazinyl substituted by $R^7$ or wherein $R^7$ is (C₅–C₇)cycloalkyl, preferably cyclohexyl, or wherein

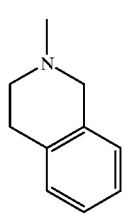

Z is wherein $R^8$ is preferably —OH

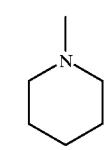

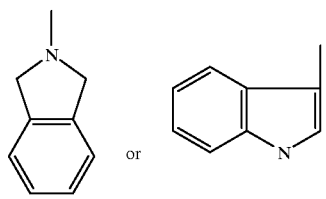

in position 4.

Test results for compounds according to the invention:

The receptor affinity for the $NK_1$-receptor (substance P-receptor) was determined on intact human lymphoblastoma cells (IM-9) which express $NK_1$-receptors, and the displacement of $^{125}I$ labelled substance P was measured.

The $IC_{50}$ or $K_i$ values thus obtained are:

| Compound Example No. | $IC_{50}$ [nM] | $K_i$ [nM] |
|---|---|---|
| 001 | | 333 |
| 002 | | 909 |
| 003 | | 800 |
| 019 | | 580 |
| 020 | | 520 |
| 022 | | 154 |
| 023 | | 108 |
| 026 | | 7 |
| 027 | | 111 |
| 028 | | 102 |
| 029 | | 119 |
| 030 | | 90 |
| 031 | | 93 |
| 032 | | 23 |
| 034 | | 38 |
| 035 | | 16 |
| 036 | | 18 |
| 039 | | 15 |
| 049 | | 37 |
| 053 | | 5 |
| 054 | | 20 |
| 057 | | 64 |
| 058 | | 23 |
| 061 | | 851 |
| 062 | | 276 |
| 064 | | 273 |
| 065 | | 7 |
| 066 | | 23 |
| 067 | | 14 |
| 068 | | 3 |
| 069 | | 16 |
| 075 | | 700 |
| 078 | | 250 |
| 079 | | 46 |
| 080 | | 43 |
| 081 | | 90 |
| 082 | | 52 |
| 083 | | 209 |
| 086 | | 368 |
| 089 | | 80 |
| 091 | | 2 |
| 096 | | 185 |
| 097 | | 300 |
| 105 | | 78 |
| 107 | | 250 |
| 108 | | 34 |
| 110 | | 28 |
| 111 | | 12 |
| 112 | | 1000 |
| 113 | | 403 |
| 114 | | 490 |
| 115 | | 30 |
| 116 | | 24 |

-continued

| Compound Example No. | IC$_{50}$ [nM] | K$_i$ [nM] |
| --- | --- | --- |
| 117 |  | 15 |
| 120 |  | 36 |
| 121 |  | 124 |
| 123 |  | 600 |
| 142 |  | 650 |
| 146 |  | 115 |
| 147 |  | 190 |
| 148 |  | 286 |
| 150 |  | 717 |
| 151 |  | 215 |
| 156 |  | 479 |
| 158 |  | 905 |
| 166 |  | 150 |
| 167 |  | 1000 |
| 169 |  | 888 |
| 170 |  | 84 |
| 171 |  | 898 |
| 172 |  | 173 |
| 175 |  | 230 |
| 176 |  | 92 |
| 177 |  | 10 | intranasal route or by inhalation, transdermally, optionally with the aid of iontophoresis or enhances known from the literature, and by oral route.

For parenteral use the compounds of formula I or the physiologically acceptable salts thereof, optionally together with conventional substances such as solubilisers, emulsifiers or other adjuvants, may be made into solutions, suspensions or emulsions. The solvents may be, for example: water, physiological saline solutions or alcohols, e.g. ethanol, propandiol or glycerol, sugar solutions such as glucose or mannitol solutions or a mixture of various solvents.

In addition, the compounds may be administered by means of implants, e.g. of polylactide, polyglycolide or polyhydroxybutyric acid or intranasal preparations. The compounds according to the invention may be prepared by methods which are generally known. One method of synthesis is shown in the following scheme. The symbols A, Z, B, $R^1$, $R^2$, $R^3$, $R^{12}$ and m used therein are defined as herein before.

SCHEME 1

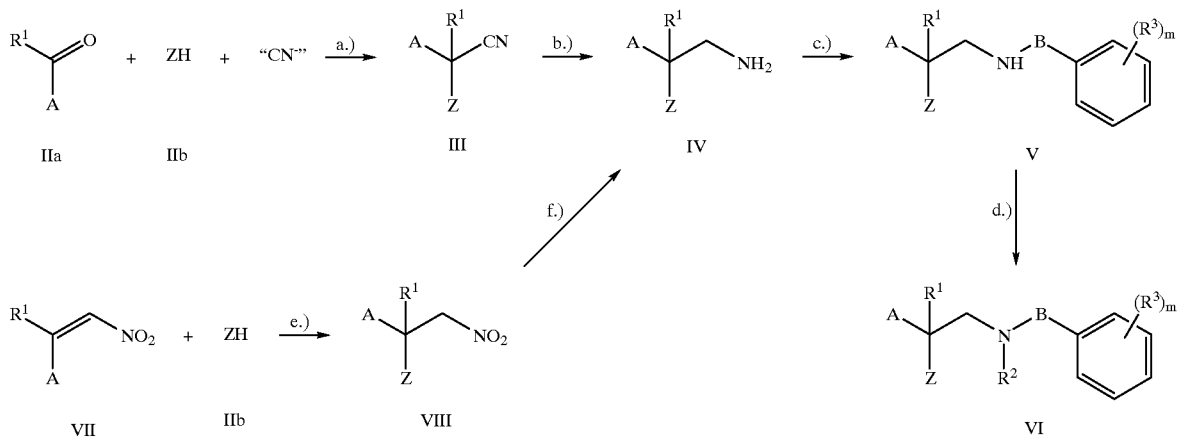

The compounds according to the invention are valuable neurokinin (tachykinin)-antagonists which have both substance P-antagonism and also neurokinin A- or neurokinin B-antagonistic properties. They are useful for the treatment and prevention of neurokinin-mediated diseases such as respiratory complaints, e.g. asthma, bronchitis, rhinitis, coughs or expectoration as well as inflammatory eye diseases such as conjunctivitis, inflammatory skin diseases such as dermatitis and urticaria, inflammatory intestinal disorders such as ulcerative colitis or Crohn's disease, other inflammatory diseases such as polyarthritis or osteoarthritis and pain (e.g. migraine or vascular headaches) and vomiting.

The invention therefore also relates to the use of the compounds according to the invention as remedies and pharmaceutical preparations which comprise these compounds. They are preferably used in humans. The compounds according to the invention may be administered by intravenous, subcutaneous, intramuscular, intraperitoneal or By reacting corresponding carbonyl compounds IIa with suitably substituted amines IIb and "cyanide sources", normally with the addition of acidic compounds, initially in step a) aminonitriles III are prepared with an amine component Z. The methods of aminonitrile synthesis known in the literature may be used. The cyanide sources used may be potassium cyanide, sodium cyanide, trimethysilylcyanide, acetonecyanohydrin and others: potassium cyanide is preferred. The acid compounds used may be acetic acid, citric acid, inorganic acids, acid salts such as sodium bisulphite, potassium bisulphite and others; hydrochloric acid is preferred. The solvents used are preferably solvents such as methanol, ethanol, diethylether, tert.-butylmethylether, tetrahydrofuran, dioxan, methylenchloride or acetonitrile, including mixtures with water. Preferably, diethylether, tetrahydrofuran and ethanol, as well as mixtures thereof, are used in admixture with water. The reaction may be carried out at temperatures from −10 C to 40 C, preferably at temperatures in the range of 0 C to room temperature. If trimethylsilylcyanide is used as the "cyanide source", the work is preferably carried out with ethers in the absence of water and in this case zinc iodide is preferably used as the acid compound. The aminonitriles III may also be synthesised, as known in the literature, via the intermediate step of an imine or immonium salt, which can be obtained from the carbonyl compound hIa and the amine IIb, by the addition of cyanide. Similarly, a cyanohydrin may be prepared by known methods, first from the carbonyl compound IIa with cyanide, and this cyanohydrin can then react with the amine IIb to form the aminonitrile III.

The aminonitriles III are reduced in step b) to the diamines IV. The methods conventionally used for reducing nitriles to amines may be used for this step. Catalytic hydrogenation, preferably with Raney-nickel as catalyst, preferably in the presence of ammonia, and reduction with borane-dimethylsulfide complex, borane-tetrahydrofuran complex, sodium borohydride, preferably in the presence of catalysts such as cobalt chloride or Raney-nickel, with lithium aluminium hydride, particularly in the presence of catalysts such as aluminium chloride, with diisobutylaluminium hydride and with alane or lithium aluminium hydride in the presences of an equivalent amount of conc. sulphuric acid are suitable. The use of lithium aluminium hydride in the presence of an equivalent amount of conc. sulphuric acid is preferred. The solvents used are ethers, preferably diethylether, possibly in admixture with tetrahydrofuran. The reaction temperature may be in the range from −78 C to reflux temperature and the work is preferably done at temperatures of −5 C to 10 C.

Alternatively, the diamines IV may also be obtained by adding the amine IIb to a nitroolefin VII (step e)) using methods described in the literature and subsequently reducing the nitro group, again using methods known from the literature (step f)).

If B denotes a group —C(O)—NH—, the diamine IV in step c) is reacted with a corresponding isocyanate. Inert solvents such as methylene chloride, chloroform, diethylether, tert-butylmethylether, tetrahydrofuran, dioxan, petroleum ether, toluene, xylene and acetonitrile may be used, but preferably methylene chloride is used. The reaction is carried out at temperatures between −20 C and 40 C preferably at ambient temperature.

If B denotes a group —C(O)—, —C(O)—CH$_2$—or —C(O)—CH$_2$—CH$_2$—, the diamine IV is coupled with a carboxylic acid

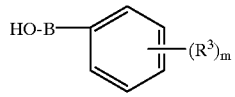

in step c) to form the amide. The methods conventionally used in preparative chemistry, including, in particular, peptide chemistry, are used for this. The carboxylic acid is activated in the form of its acid chloride or activation is carried out using carbonyldiimidazole, dicyclohexylcarbodiimide, diphenylphosphorylazide, diisovalerylchloride, diethylphosphorylcyanide and other activating reagents known from peptide chemistry. It is preferred to use diethylphosphorylcyanide. The activation and coupling are preferably carried out in the presence of auxiliary basis such as triethylamine, pyridine etc., or in the case of acid chlorides aqueous alkali metal hydroxide solution. Preferable, triethylamine is used. The reaction may be carried out in solvents such as dimethylformamide, tetrahydrofuran or acetonitrile, dimethylformamide being preferred. The work is done at temperatures between −10 C and 40 C preferably at ambient temperature.

If B represents a group —CH(R$^{12}$)— or —CH$_2$—CH$_2$—, the diamine IV in step c) may be reacted, using methods known from the literature, with

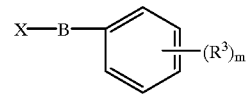

wherein X is a leaving group such as chlorine, bromine, iodine, O-tosylate, O-triflate, O-mesylate etc.

However, it is also possible initially to prepare an amide, as described above, by reacting the diamine IV with a carboxylic acid. In a subsequent step the group B —C(O)— or —C(O)—CH$_2$— of the amide can then be reduced to a group B —CHR$^{12}$— wherein R$^{12}$ equals H or —CH$_2$—CH$_2$—. The methods known from the literature for reducing amides may be used for this step, such as catalytic hydrogenation or reduction with lithium aluminium hydride, with sodium borohydride in the presence of cobalt chloride or acetic acid or trifluoroacetic acid or with borane or borane-tetrahydrofuran complex or borane/dimethylsulfide complex. Preferably, catalytic hydrogenation is carried out or sodium borohydride is used with trifluoroacetic acid or borane/dimethylsulfide complex in tetrahydrofuran or dioxane.

The reaction with the above-mentioned boron reagents is carried out at temperatures ranging from −10° C. to about 100° C., preferably at the boiling temperature of the solvent.

Preferably, the diamine IV in step c) may also be reacted with a corresponding carbonile compound

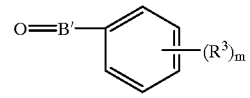

wherein B' is =C(R$^{12}$)— or =CH—CH$_2$—, according to methods known from the literature, to obtain an imine which can be reduced. to V. The imine is preferably prepared in inert solvents such as benzene, toluene or xylene (or other solvents suitable for the azeotropic removal of the water) using a water separator; or in methylene chloride, tetrahydrofuran, dioxane or tert.butyl-methylether in the presence of a water binding agent such as molecular sieves and the like, or else in alcohols. The imine may be reduced using reducing agents such as sodium borohydride, sodium cyanoborohyride, lithium aluminium hydride, zinc and hydrochloric acid, formic acid and hydrogen in the presence of metal catalysts.

Preferably, IV in step c) is reacted directly with the above-mentioned carbonyl compound in a reductive amination to obtain V. Sodium borohydride, sodium cyanoborohydride, lithium aluminium hydride, zinc and hydrochloric acid, formic acid and hydrogen in the presence of metal catalysts are suitable reducing agents. The reducing agent preferably used is sodiumcyanoborohydride in a solvent such as methanol, ethanol or isopropanol. The pH of the reaction mixture is preferably adjusted to a level of 7–8 using ethereal or ethanolic hydrochloric acid. The reaction temperature is selected between −10° C. and 40° C. and preferably the work is done at room temperature.

The remarks made above for step c) also apply to the insertion of group R$^2$ in step d).

EXAMPLE 1

3,5-Bistrifluoromethylbenzyl-[2-(2-methoxyphenyl)-2-4-phenylpiperazine-1-yl)-ethyl]-amine a) (2-Methoxyphenyl)-(4-phenylpiperazine-1-yl)-acetonitrile 6.5 g (40 mmol) of 1-phenylpiperazine are dissolved in 40 ml of 1N-hydrochloric acid and mixed with a solution of 5.4 g (40 mmol) of 2-methoxybenzaldehyde in 60 ml of ether. The mixture is cooled to 0° C., a solution of 2.5 g (40 mmol) potassium cyanide in 30 ml of water is slowly added dropwise, with stirring, and the mixture is stirred overnight at ambient temperature. Then the organic phase is separated off (any product already precipitated is removed by suction filtration beforehand). The aqueous phase is wasted three times with 50 ml of ether, the organic phases are combined and dried over sodium sulfate. The solvent is eliminated in vacuo and the residue is stirred with cyclohexane and suction filtered. 9.3 g of (2-Methoxyphenyl)-(4-phenylpiperazine-1-yl)-acetonitrile are obtained (76% yield) as an almost colourless solid.

b) 2-(2-Methoxyphenyl)-(4-phenylpiperazine-1-yl)-ethylamine 2.3 g (60 mmol) of Lithium aluminium hydride are suspended in 100 ml of ether under a nitrogen atmosphere and cooled to about −10° C. 1.6 ml (30 mmol) of conc. sulphuric acid are carefully added dropwise thereto, with further cooling, and the resulting mixture is stirred for 1.5 hours at about −5° C. Then a solution of 9.2 g (30 mmol) of (2-methoxyphenyl)-(4-phenylpiperazine-1-yl)-acetonitrile in 50 ml of tetrahydrofuran is slowly added dropwise. The mixture is allowed to come up to ambient temperature and is then refluxed for about 10 minutes. It is then allowed to cool and stirred overnight at ambient temperature. A mixture of 8 ml of tetrahydrofuran and 8 ml of water is then added, initially very carefully, to the grey suspension, whilst cooling with ice, and then 165 ml of 2N hydrochloric acid are added. The reaction mixture is then washed twice with 70 ml of ether and the ethereal phases are discarded. 18.2 g of Seignette salt and 45 ml of conc. sodium hydroxide solution are then added. The mixture is extracted four times with 70 ml of ether, the combined organic phases are dried over sodium sulfate and the solvent is eliminated in vacuo. 8.6 g of 2-(2-methoxyphenyl)-(4-phenylpiperazine-1-yl)-ethylamine are obtained (92% yield) as a yellowish oil. There is no additional purification before the further reactions.

c) 3,5-Bistrifluoromethylbenzyl-[2-(2-methoxyphenyl)-2-(4-phenylpiperazine-1-yl)-ethyl]-amine 625 mg (2 mmol) of 2-(2-methoxyphenyl)-(4-phenylpiperazine-1-yl)-ethylamine are dissolved in 10 ml of methanol and mixed with 346 ml (2.1 mmol) of 3,5-bistrifluoromethylbenzaldehyde. 190 mg (3 mmol) of sodium cyanoborohydride are added whilst cooling with ice and the mixture is then stirred for about 30 minutes more at 0° C., then overnight at ambient temperature. Is then made slightly acidic with 2N hydrochloric acid, whilst cooling with ice, and the reaction mixture is evaporated down in vacuo. 70 ml of water are added, the mixture is made alkaline with 2N sodium hydroxide solution (pH about 9) and extracted with ether (3×50 ml). The combined organic phases are dried over sodium sulfate and the solvent is eliminated in vacuo. The residue is chromatographed with ethyl acetate and methanol 7:3 over silica gel. The fractions which are uniform according to TLC are combined and freed from solvent in vacuo. The residue is taken up in about 2 ml of isopropanol and the 3,5-bistrifluoromethylbenzyl-[2-(2-methoxyphenyl)-2-(4-phenylpiperazine-1-yl)-ethyl]-amine is precipitated therefrom in the form of the hydrochloride using ethereal hydrochloric acid and diisopropyl ether. The hydrochloride is suction filtered, washed with diisopropyl ether and dried at about 50° C. in vacuo. 950 mg of the substance are obtained in the form of a colourless solid (yield 73%).

Examples 2 to 57 are prepared analogously.

EXAMPLE 2

N-3,5-Bistrifluoromethylbenzyl-N-[2-(2-methoxyphenyl)-2-(4-phenylpiperazine-1-yl)-ethyl]-acetamide 162 mg (0.25 mmol) of 3,5-bistrifluoromethylbenzyl-[2-(2-methoxyphenyl)-2-(4-phenylpiperazine-1-yl)-ethyl]-amine (for preparation see Example 1) are dissolved in 10 ml of THF and mixed with 175 ml of triethylamine (1.25 mmol). 21 ml (0.3 mmol) of acetylchloride are added dropwise thereto, whilst coolling with ice, the mixture is heated to ambient temperature and then refluxed for about 2 hours. The reaction mixture is then evaporated down in vacuo, stirred with 40 ml of water and extracted with 3×20 ml of ethyl acetate. The organic phases are combined, evaporated down and the residue is chromatographed over silica gel with ethyl acetate/cyclohexane/methanol 60:30:5. The fractions which are uniform according to TLC are combined and freed from solvents in vacuo. The residue is dissolved in a little isopropanol and the N-3,5-bistrifluoromethylbenzyl-N-[2-(2-methoxyphenyl)-2-(4-phenylpiperazine-1-yl)-ethyl]-acetamide is precipitated therefrom in the form of the hydrochloride using ethereal hydrochloric acid and diisopropyl ether. The substance is suction filtered, washed with diisopropyl ether and dried in vacuo at about 50° C. 110 mg of the hydrochloride are obtained in the form of a light beige solid (yield 67%).
MS: $(M+H)^+=580.2$ (Base).

EXAMPLE 3

3,5-Bistrifluoromethylbenzyl-[2-phenyl-2-(4-phenylpiperazine-1-yl)-ethyl]-amine

EXAMPLE 4

3,5-Bistrifluoromethylbenzyl-[2-phenyl-2-(4-(2,6-dimethylphenyl)piperazine-1-yl)-ethyl]-amine

EXAMPLE 5

3,5-Bistrifluoromethylbenzyl-[2-phenyl-2-(4-(2-hydroxyphenyl)piperazine-1-yl)-ethyl]-amine

EXAMPLE 6

3,5-Bistrifluoromethylbenzyl-[2-phenyl-2-(4-(2-methoxyphenyl)piperazine-1-yl)-ethyl]-amine

EXAMPLE 7

3,5-Bistrifluoromethylbenzyl-[2-phenyl-2-(4-(3-methoxyphenyl)piperazine-1-yl)-ethyl]-amine

EXAMPLE 8

3,5-Bistrifluoromethylbenzyl-[2-phenyl-2-(4-(4-methoxyphenyl)piperazine-1-yl)-ethyl]-amine

EXAMPLE 9

3,5-Bistrifluoromethylbenzyl-[2-phenyl-2-(4-(2,4-dimethoxyyhenyl)piperazine-1-yl)-ethyl]-amine The preparation is analogous to Example 1 but the amino nitrile is reduced as follows:

3.1 g (9 mmol) of phenyl-(4-(2,4-dimethoxyphenyl) piperazine-1-yl)-acetonitrile are dissolved in 35 ml of THF and 35 ml of methanol and combined with 5 g of ammonia and about 5 g of Raney-Nickel (methanol-moist). Reduction is carried out at 60° C. under 5 bar with hydrogen. The catalyst is then removed by filtration over activated charcoal and kieselgur and the solvent is distilled off under reduced pressure. The residue is taken up with a little methylene chloride and a hydrochloride is precipitated therefrom with ethereal hydrochloric acid. The precipitate is suction filtered, the substance is dissolved in a little chloroform/methanol 3:1 and chromatographed with chloroform/methanol/conc. ammonia solution 180:10:1. The fractions which are uniform according to TLC are combined and freed from solvent in vacuo. The residue is taken up in a little methylene chloride and 3,5-bistrifluoromethylbenzyl-[2-phenyl-2-(4-(2,4-dimethoxyphenyl)-piperazine-1-yl)-ethyl]-amine is precipitated therefrom in the form of the hydrochloride using ethereal hydrochloric acid. 1 g of the substance is obtained as a light brown solid (yield 25%).

EXAMPLE 10

3,5-Bistrifluoromethylbenzyl-[2-phenyl-2-(4-(3,5-dimethoxyphenyl)-piperazine-1-yl)-ethyl]-amine

EXAMPLE 11

3,5-Bistrifluoromethylbenzyl-[2-phenyl-2-(4-(2-(methylthio)phenyl)-piperazine-1-yl)-ethyl]-amine

EXAMPLE 12

3,5-Bistrifluoromethylbenzyl-[2-phenyl-2-(4-(2-fluorophenyl-piperazine-1-yl)-ethyl]-amine

EXAMPLE 13

3,5-Bistrifluoromethylbenzyl-[2-phenyl-2-(4-(4-fluorophenyl)-piperazine-1-yl)-ethyl]-amine

EXAMPLE 14

3,5-Bistrifluoromethylbenzyl-[2-phenyl-2-(4-(4-trifluoromethylphenyl-piperazine-1-yl)-ethyl]-amine

EXAMPLE 15

3,5-Bistrifluoromethylbenzyl-[2-phenyl-2-(4-(4-nitrophenyl-piperazine-1-yl)-ethyl]-amine

EXAMPLE 16

3,5-Bistrifluoromethylbenzyl-[2-phenyl-2-(4-(4-chlorobenzyl)-piperazine-1-yl)-ethyl]-amine

EXAMPLE 17

3,5-Bistrifluoromethylbenzyl-[2-phenyl-2-(4-(3,4-methylenedioxybenzyl)-piperazine-1-yl)-ethyl]-amine Prepared analogously to Example 9.

EXAMPLE 18

3,5-Bistrifluoromethylbenzyl-[2-phenyl-2-(4-(9-fluorenyl)-piperazine-1-yl)-ethyl]-amine

EXAMPLE 19

3,5-Bistrifluoromethylbenzyl-[2-(2-methoxyphenyl)-2-(4-(2-methylphenyl)-piperazine-1-yl)-ethyl]-amine

EXAMPLE 20

3,5-Bistrifluoromethylbenzyl-[2-(2-methoxyphenyl)-2-(4-(2,3-dimethylphenyl)-pierazine-1-yl)-ethyl]-amine

EXAMPLE 21

3,5-Bistrifluoromethylbenzyl-[2-(2-methoxyphenyl)-2-(4-(2-chlorophenyl)-piperazine-1-yl)-ethyl]-amine

EXAMPLE 22

3,5-Bistrifluoromethylbenzyl-[2-(2-methoxyphenyl)-2-(4-benzylpiperazine-1-yl)-ethyl]-amine

EXAMPLE 23

3,5-Bistrifluoromethylbenzyl-[2-(2-methoxyphenyl)-2-(4-(1-phenylethyl)-piperazine-1-yl)-ethyl]-amine

EXAMPLE 24

3,5-Bistrifluoromethylbenzyl-[2-(2-methoxyphenyl)-2-(4-benzhydrylpiperazine-1-yl)-ethyl]-amine

EXAMPLE 25

3,5-Bistrifluoromethylbenzyl-[2-phenyl-2-(4-(2-phenylethyl)-piperazine-1-yl)-ethyl]-amine

EXAMPLE 26

3,5-Bistrifluoromethylbenzyl-[2-(2-methoxyphenyl)-2-(4-2-phenylethyl)-piperazine-1-yl)-ethyl]-amine

FAB-MS: $(M+H)^+=566$.

EXAMPLE 27

3,5-Bistrifluoromethylbenzyl-[2-(2-methoxyphenyl)-2-(4-(3,4-methylenedioxybenzyl-piperazine-1-yl)-ethyl]-amine

EXAMPLE 28

3,5-Bistrifluoromethylbenzyl-[2-(2-methoxyphenyl)-2-(4-(2-pyridyl)-piperazine-1-yl)-ethyl]-amine

EXAMPLE 29

3,5-Bistrifluoromethylbenzyl-[2-(2-methoxyphenyl)-2-(4-(2-quinolinyl)-piperazine-1-yl)-ethyl]-amine

EXAMPLE 30

3,5-Bistrifluoromethylbenzyl-[2-phenyl-2-(4-methylperazine-1-yl)-ethyl]-amine

EXAMPLE 31

3,5-Bistrifluoromethylbenzyl-[2-(2-methoxyphenyl)-2-(4-methylpiperazine-1-yl)-ethyl]-amine

EXAMPLE 32

3,5-Bistrifluoromethylbenzyl-[2-(2-methoxyphenyl)-2-(4-(1-propyl)-piperazine-1-yl)-ethyl]-amine

EXAMPLE 33

3,5-Bistrifluoromethylbenzyl-[2-phenyl-2-[4-allylpiperazine-1-yl)-ethyl]-amine

EXAMPLE 34

3,5-Bistrifluoromethylbenzyl-[2-(2-methoxyphenyl)-2-(4-(2-propyl)-piperazine-1-yl)-ethyl]-amine

EXAMPLE 35

3,5-Bistrifluoromethylbenzyl-[2-(2-methoxyphenyl)-2-(4-cyclopentylpiperazine-1-yl)-ethyl]-amine

EXAMPLE 36

3,5-Bistrifluoromethylbenzyl-[2-phenyl-2-(4-cyclohexyl-piperazine-1-yl)-ethyl]-amine

EXAMPLE 37

2-Methoxybenzyl-[2-phenyl-2-(4-cyclohexylpiperazine-1-yl)-ethyl]-amine

EXAMPLE 38

2-Chlorobenzyl-[2-phenyl-2-(4-cyclohexylpiperazine-1-yl)-ethyl]-amine

EXAMPLE 39

3,5-Bistrifluoromethylbenzyl-[2-(2-methoxyhenyl-2-(4-cyclohexylpiperazine-1-yl)-ethyl]-amine

EXAMPLE 40

1-(3,4-Dichlorophenyl)-2'-(2-methoxyphenyl)-2'-(4-cyclohexylpiperazine-1-yl)-diethylamine

EXAMPLE 41

3,5-Bistrifluoromethylbenzyl-[2-(3-methoxyphenyl)-2-(4-cyclohexylpiperazine-1-yl)-ethyl]-amine

EXAMPLE 42

3,5-Bistrifluoromethylbenzyl-(2-(4-methoxyphenyl)-2-(4-cyclohexylpiperazine-1-yl)-ethyl]-amine

EXAMPLE 43

3,5-Bistrifluoromethylbenzyl-[2-(3,4,5-trimethoxyphenyl)-2-(4-cyclohexylpiperazine-1-yl)-ethyl]-amine

EXAMPLE 44

3,5-Bistrifluoromethylbenzyl-[2-(4-methylphenyl)-2-(4-cyclohexylpiperazine-1-yl)-ethyl]-amine

EXAMPLE 45

3,5-Bistrifluoromethylbenzyl-[3-phenyl-2-(4-cyclohexylpiperazine-1-yl)-propyl]-amine

EXAMPLE 46

3,5-Bistrifluoromethylbenzyl-[3,3-diphenyl-2-(4-cyclohexylpiperazine-1-yl)-propyl]-amine

EXAMPLE 47

3,5-Bistrifluoromethylbenzyl-[2-(2-naphthyl)-2-(4-cyclohexylpiperazine-1-yl)-ethyl]-amine

EXAMPLE 48

3,5-Bistrifluoromethylbenzyl-[2-(4-chlorophenyl)-2-(4-cyclohexylpiperazine-1-yl)-ethyl]-amine

EXAMPLE 49

3,5-Bistrifluoromethylbenzyl-[2-(3,4-dichlorophenyl)-2-(4-cyclohexylpiperazine-1-yl-]-ethyl]-amine

EXAMPLE 50

3,5-Bistrifluoromethylbenzyl-[2-(4-fluorophenyl-2-(4-cyclohexylpiperazine-1-yl)-ethyl]-amine

EXAMPLE 51

3,5-Bistrifluoromethylbenzyl-[2-(2-trifluoromethylhenyl-2-(4-cyclohexylpiperazine-1-yl)-ethyl]-amine

EXAMPLE 52

3,5-Bistrifluoromethylbenzyl-[2-(3,5-bistrifluoromethylphenyl)-2-(4-cyclohexylpiperazine-1-yl)-ethyl]-amine

EXAMPLE 53

3,5-Bistrifluoromethylbenzyl-[2-(2-methoxyphenyl)-2-4-cycloheptylpiperazine-1-yl)-ethyl]-amine

EXAMPLE 54

3,5-Bistrifluoromethylbenzyl-[2-(2-methoxyphenyl)-2-(4-(2-cyclohexylethyl)-piperazine-1-yl)-ethyl]-amine

EXAMPLE 55

3,5-Bistrifluoromethylbenzyl-[2-(2-methoxyphenyl)-2-(4-(2-indanyl)-piperazine-1-yl)-ethyl]-amine

EXAMPLE 56

3,5-Bistrifluoromethylbenzyl-[2-(2-methoxyphenyl)-2-(4-(1,2,3,4-tetrahydronaphth-2-yl)-piperazine-1-yl)-ethyl]-amine

EXAMPLE 57

3,5-Bistrifluoromethylbenzyl-[2-(2-methoxyphenyl)-2-(4-(2-hydroxyethyl)-piperazine-1-yl)-ethyl]-amine

EXAMPLE 58

N-[2-(2-Methoxyphenyl)-2-(4-cyclohexylpiperazine-1-yl)-ethyl]-3,5-bistrifluoromethylbenzamide 317 mg (1 mmol) of 2-Methoxyphenyl-2-(4-cyclohexylpiperazine-1-yl)-ethylamine (prepared as described in Example 1) are combined with 272 mg (1 mmol) of 3,5-bistrifluoromethylbenzoic acid in 30 ml of DMF. The mixture is cooled to about 3° C. and combined with 501 ml (3.3 mmol) of diethylphosphorylcyanide and 1.4 ml triethylamine. After about 1 hour the ice bath is removed and the mixture is stirred overnight at ambient temperature. It is evaporated down in vacuo and the residue is stirred with a little water and 20% sodium hydrogen carbonate solution. It is suction filtered and washed thoroughly with water. The crude product is chromatographed over silica gel with ethyl acetate/methanol 1:1. The fractions which are uniform according to TLC are combined and freed from solvent in vacuo. The residue is dissolved in a little isopropanol and the N-[2-(2-methoxyphenyl)-2-(4-cyclohexylpiperazine-1-yl)-ethyl]-3,5-bistrifluoromethyl-benzamide is precipitated therefrom in the form of the hydrochloride using ethereal hydrochloric acid and diisopropylether. The product is suction filtered, washed with diisopropylether and dried in vacuo at about 50° C. 200 mg of the substance are obtained as a slightly beige solid (yield 32%).

EXAMPLE 59

N-[2-(2-Methoxyphenyl)-2-(4-cyclohexylpiperazine-1-yl)-ethyl]-2-phenylacetamide

Prepared analogously to Example 58.

EXAMPLE 60

N-[2-(2-Methoxyphenyl)-2-(4-cyclohexylpiperazine-1-yl)-ethyl]-2-(4-methoxyphenyl)-acetamide Prepared analogously to Example 58.

EXAMPLE 61

N-[2-(2-Methoxyphenyl-2-(4-cyclohexylpiperazine-1-yl)-ethyl]-2-(4-chlorophenyl)-acetamide Prepared analogously to Example 58.

EXAMPLE 62

N-[2-2-Methoxyphenyl)-2-4-cyclohexylpiperazine-1-yl)-ethyl-]-2-(3,4-dichlorophenyl)-acetamide Prepared analogously to Example 58.

EXAMPLE 63

N-[2-(3,4-dichlorophenyl)-2-(4-cyclohexylpiperazine-1-yl)-ethyl]-2-[3-(2-propyloxy)-phenyl]-acetamide Prepared analogously to Example 58.

EXAMPLE 64

N-[2-(2-Methoxyphenyl)-2-(4-cyclohexylpiperazine-1-yl)-ethyl]-2-(2-trifluoromethylphenyl)-acetamide Prepared analogously to Example 58.

EXAMPLE 65

N-[2-(2-Methoxyphenyl)-2-(4-cyclohexylpiperazine-1-yl)-ethyl]-2-(3,5-bistrifluoromethylphenyl)-acetamide Prepared analogously to Example 58.

EXAMPLE 66

2-(3,5-Bistrifluoromethylphenyl)-2'-(2-methoxyphenyl)-2'-(4-cyclohexylpiperazine-1-yl)-diethylamine 220 mg (0.4 mmol) of N-[2-(2-methoxyphenyl)-2-(4-cyclohexylpiperazine-1-yl)-ethyl]-2-(3,5-bistrifluoromethylphenyl-acetamide (prepared as in Example 65) are combined with 150 mg (4 mmol) of sodium borohydride in 2 ml of dioxane. The mixture is cooled to about 10° C. and a solution of 460 ml (6 mmol) of trifluoroacetic acid in 1 ml of dioxane is slowly added dropwise thereto. The mixture is then refluxed for 3 hours, cooled again, mixed with 20 ml of water and made alkaline with sodium carbonate. It is extracted with 3×50 ml of ether, the ethereal extract is evaporated down and the residue is chromatographed over silica gel with ethyl acetate/methanol 1:1. The fractions which are uniform according to TLC are combined and freed from solvent in vacuo. The residue is dissolved in a little isopropanol and the 2-(3,5-bistrifluoromethylphenyl-21-(2-methoxyphenyl)-2'-(4-cyclohexylpiperazine-1-yl)-diethylamine is precipitated therefrom in the form of the hydrochloride using ethereal hydrochloric acid and diisopropylether. The product is suction filetered, washed with diisopropylether and dried at about 50° C. in vacuo. 75 mg of the substance are obtained as a slightly beige solid (yield 28%).

EXAMPLE 67

N-[2-(2-Methoxyphenyl)-2-(4-cyclohexylpiperazine-1-yl)-ethyl]-3,5-bistrifluoromethylbenzamide Prepared analogously to Example 66.

EXAMPLE 68

N-[2-(2-Methoxyphenyl)-2-(4-cycloheptylpiperazine-1-yl)-ethyl]-2-(3,5-bistrifluoromethyl-phenyl)-acetamide Prepared analogously to Example 58.

EXAMPLE 69

2-(3,5-Bistrifluoromethylphenyl)-2'-(2-methoxyphenyl)-2'-(4-cycloheptylpiperazine-1-yl)-diethylamine Prepared analogously to Example 66.

EXAMPLE 70

N-[2-(3,4-dichlorophenyl)-2-(4-(2-phenylethyl)-piperazine-1-yl)-ethyl]-2-[3-(2-propyloxy)-phenyl]-acetamide Prepared analogously to Example 58.

EXAMPLE 71

N-[2-(2-Methoxyphenyl)2-(4-(2-indanyl)piperazine-1-yl)-ethyl]-2-(3,5-bistrifluoromethylphenyl)-acetamide Prepared analogously to Example 58.

EXAMPLE 72

N-[2-(2-Methoxythenyl-2-(4-(1,2,3, 4-tetrahydronaphth-2-yl)piperazine-1-yl)-ethyl]-2-(3,5-bistrifluoromethylphenyl)-acetamide Prepared analogously to Example 58.

EXAMPLE 73

3,5-Bistrifluoromethylbenzyl-[2-(2-methoxyphenyl)-
2-(4-cyclohexylhomopiperazine-1-yl)-ethyl]-amine Prepared analogously to Example 1.

EXAMPLE 74

N-[2-(2-Methoxyphenyl)-2-(4-
cyclohexylhomopiperazine-1-yl)-ethyl]-2-(3,5-
bistrifluoromethyl-phenyl)-acetamide Prepared analogously to Example 58.

EXAMPLE 75

N-[2-(2-Methoxyphenyl)-2-piperidin-1-yl-ethyl]-3,
5-bistrifluoromethylbenzamide

Prepared analogously to Example 58.

EXAMPLE 76

N-[2-(2-Methoxyphenyl)-2-piperidin-1-yl-ethyl]-2-
phenylacetamide

Prepared analogously to Example 58.

EXAMPLE 77

2-Phenyl-2'-(2-methoxyphenyl)-2'-piperidin-1-yl-
diethylamine 1.2 g (3.4 mmol) of N-[2-(2-methoxyphenyl)-2-piperidin-1-yl-ethyl]-2-phenylacetamide (prepared as in Example 76) are combined, in 20 ml of THF, with 0.5 ml (5.1 mmol) of borane-dimethylsulfide complex in THF. The mixture is stirred for about 15 minutes at ambient temperature and then refluxed for about 5 hours. The reaction mixture is then cooled with an ice bath and about 10 ml of methanol are carefully added. It is evaporated down, the residue is combined with 50 ml of water and 20 ml of 20% sodium hydrogen carbonate solution and extracted with 3×50 ml of ether. The ether extract is dried over sodium sulfate and solvent is eliminated in vacuo. The crude product is chromatographed over silica gel using ether acetate/methanol 1:1. The fractions which are uniform according to TLC are combined and freed from solvent in vacuo. 620 mg of 2-phenyl-2'-(2-methoxyphenyl)-2'-piperidin-1-yl-diethylamine are obtained (yield 54%).

EXAMPLE 78

N-[2-(2-Methoxyphenyl)-2-piperidin-1-yl-ethyl]-2-
(3,5-bistrifluoromethylphenyl)acetamide Prepared analogously to Example 58.

EXAMPLE 79

2-(3,5-Bistrifluoromethylphenyl)-2'-(2-methoxyphenyl)-
2'-piperidine-1-yl-diethylamine Prepared analogously to Example 77 from N-[2-(2-Methoxyphenyl)-2-piperidin-1-yl-ethyl]-2-(3,5-bistrifluoromethylphenyl)acetamide (for preparation see Example 78).

EXAMPLE 80

3,5-Bistrifluoromethylbenzyl-[2-(2-methoxyphenyl)-
2-(2-methylpiperidine-1-yl)-ethyl]-amine Prepared analogously to Example 1.

EXAMPLE 81

3,5-Bistrifluoromethylbenzyl-[2-2-methoxyphenyl-
2-(3-methylpiperidine-1-yl)-ethyl]-amine Prepared analogously to Example 1.

EXAMPLE 82

3,5-Bistrifluoromethylbenzyl-[2-(2-methoxyphenyl)-
2-(4-methylpiperidine-1-yl)-ethyl]-amine Prepared analogously to Example 1.

EXAMPLE 83

3,5-Bistrifluoromethylbenzyl-[2-(2-methoxyphenyl)-
2-(3,5-dimethylpiperidine-1-yl)-ethyl]-amine Prepared analogously to Example 1.

EXAMPLE 84

3,5-Bistrifluoromethylbenzyl-[2-(2-methoxyphenyl)-
2-(4-hydroxypiperidine-1-yl)-ethyl]-amine Prepared analogously to Example 1.

EXAMPLE 85

3,5-Bistrifluoromethylbenzyl-[2-(2-methoxyphenyl)-
2-(3-phenylpiperidine-1-yl)-ethyl]-amine Prepared analogously to Example 1. The hydrochloride is not precipitated but instead the crude base is chromatographed.

0.8 g of the crude base are chromatographed over 100 g of silica gel, initially with 300 ml of cyclohexane/ethyl acetate 7:3 and then with 300 ml of ethyl acetate/cyclohexane/methanol 60:35:5. The fractions which are uniform according to TLC are combined and a first fraction (0.15 g of yellow oil) is obtained having a low retention time, a third fraction 0.15 g of yellow oil having a higher retention time and a second, intermediate fraction 0.28 g of yellow oil which is a mixture of the substances contained in fractions 1 and 3. Fraction 1 is dissolved in 5 ml of acetone and 3,5-bistrifluoromethylbenzyl-[2-(2-methoxyphenyl)-2-(3-phenylpiperidine-1-yl)-ethyl]-amine is precipitated therefrom in the form of the hydrochloride using ethereal hydrochloric acid and diisopropylether. 0.12 g of the substance are obtained as a creamy coloured solid (yield 10%).

EXAMPLE 86

3,5-Bistrifluoromethylbenzyl-[2-(2-methoxyphenyl)-
2-(3-phenylpiperidine-1-yl)-ethyl]-amine
Diastereomers from Example 85

The same procedure is used as for Example 85 and Fraction 3 is converted into the hydrochloride. 90 mg of creamy coloured solid are obtained (yield 7%).

EXAMPLE 87

3,5-Bistrifluoromethylbenzyl-[2-(2-methoxyrhenyl)-
2-(4-phenylpiperidine-1-yl)-ethyl]-amine Prepared analogously to Example 1.

EXAMPLE 88

3,5-Bistrifluoromethylbenzyl-[2-(2-methoxyphenyl)-
2-(4-benzylpiperidine-1-yl)-ethyl]-amine Prepared analogously to Example 1.

EXAMPLE 89

3,5-Bistrifluoromethylbenzyl-[2-(2-methoxyphenyl)-2-(4-cyclohexylpiperidine-1-yl)-ethyl]-amine Prepared analogously to Example 1.

EXAMPLE 90

3,5-Bistrifluoromethylbenzyl-[2-(2-methoxyphenyl)-2-(3-hydroxypiperidine-1-yl)-ethyl]-amine Prepared analogously to Example 1.

EXAMPLE 91

3,5-Bistrifluoromethylbenzyl-[2-(2-methoxyphenyl)-2-(4-)piperidin-1-yl)-piperidin-1-yl)-ethyl]-amine Prepared analogously to Example 1.

EXAMPLE 92

N-[2-(2-Methoxyphenyl)-2-(4-(piperidine-1-yl)piperidine-1-yl)-ethyl]-3,5-bistrifluoromethyl-benzamide Prepared analogously to Example 58.

EXAMPLE 93

N-[2-(2-Methoxyphenyl)-2-(4-(piperidine-1-yl)piperidine-1-yl)-ethyl)-2-(3,5-bistrifluoromethyl-phenyl)-acetamide Prepared analogously to Example 58.

EXAMPLE 94

N-[2-(3,4-Dichlorophenyl)-2-(4-(piperidine-1-yl)piperidine-1-yl)-ethyl]-2-(3,5-bistrifluoromethylphenyl)-acetamide Prepared analogously to Example 58.

EXAMPLE 95

3,5-Bistrifluoromethylbenzyl-(2-(3,4-dichlorophenyl)-2-(4-(piperidine-1-yl)-piperidine-1-yl)-ethyl]-amine Prepared analogously to Example 1.

EXAMPLE 96

3,5-Bistrifluoromethylbenzyl-(2-phenyl-2-morpholine-4-yl-ethyl)-amine

Prepared analogously to Example 1.

EXAMPLE 97

3,5-Bistrifluoromethylbenzyl-(2-(2-methoxytphenyl)-2-(4-(3-indolyl)-piperidine-1-yl)-ethyl]-amine Prepared analogously to Example 1.

EXAMPLE 98

3,5-Bistrifluoromethylbenzyl-[2-(2-methoxyphenyl)-2-(4-(2-isoindolinyl)-piperidine-1-yl)-ethyl]-amine Prepared analogously to Example 1.

EXAMPLE 99

N-[2-(2-Methoxyphenyl)-2-(4-(2-isoindolinyl)piperidine-1-yl)-ethyl]-2-(3,5-bistrifluoromethyl-phenyl)-acetamide Prepared analogously to Example 58.

EXAMPLE 100

3,5-Bistrifluoromethylbenzyl-[2-(2-methoxyphenyl)-2-(4-(1,2,3,4-tetrahydroisoauinoline-2-yl)piperidine-1-yl)-ethyl]-amine Prepared analogously to Example 1.

EXAMPLE 101

N-[2-(2-Methoxyphenyl)-2-(4-(1,2,3,4-tetrahydroisoguinoline-2-yl-piperidine-1-yl)-ethyl]-2-(3,5-bistrifluoromethylphenyl)-acetamide Prepared analogously to Example 58.

EXAMPLE 102

N-Phenyl-N'-[2-phenyl-2-(4-methylpiperazine-1-yl)-ethyl]-urea

2-Phenyl-2-(4-methylpiperazine-1-yl)ethylamine is prepared analogously to Example 1.

482 mg (2.2 mmol) of 2-phenyl-2-(4-methylpiperazine-1-yl)ethylamine are dissolved in 10 ml of methylene chloride and mixed with 217 ml (2 mmol) of phenylisocyanate at about −5° C. The mixture is stirred for 2 hours at ambient temperature and the solvent is then eliminated in vacuo. The residue is stirred with petroleum ether (boiling temperature ranging from 40–80° C.), the precipitate is suction filtered and dried in vacuo at 50° C. 490 mg N-phenyl-N'-[2-phenyl-2-(4-methylpiperazine-1-yl-ethyl]-urea are obtained as a beige solid (yield 73%).

Examples 103–180 are prepared analogously.

EXAMPLE 103

N-2-Methoxyphenyl-N'-[2-phenyl-2-(4-methylpiperazin-1-yl)-ethyl]-urea

EXAMPLE 104

N-2-Chlorophenyl-N'-[2-phenyl-2-(4-methylpiperazine-1-yl)-ethyl]-urea

EXAMPLE 105

N-3,5-Bistrifluoromethylphenyl-N'-[2-phenyl-2-(4-methylpiperazine-1-yl)-ethyl]-urea

EXAMPLE 106

N-Phenyl-N'-[2-(2-methoxyphenyl)-2-(4-methylpiperazine-1-yl)-ethyl]-urea

EXAMPLE 107

N-3,5-Bistrifluoromethylphenyl-N'-[2-(2-methoxyphenyl)-2-(4-methylpiperazin-1-yl)-ethyl]-urea

EXAMPLE 108

N-3,5-Bistrifluoromethylphenyl-N'-[2-(2-methoxyphenyl)-2-(4-(1-propyl)piperazine-1-yl)-ethyl]-urea

EXAMPLE 109

N-3,5-Bistrifluoromethylphenyl-N'-[2-phenyl-2-(4-allylpiperazine-1-yl)-ethyl]-urea

EXAMPLE 110

N-3,5-Bistrifluoromethylphenyl-N'-[2-(2-methoxyphenyl)-2-(4-(2-propyl)piperazin-1-yl)-ethyl]-urea

EXAMPLE 111

N-3,5-Bistrifluoromethylphenyl-N'-[2-(2-methoxyphenyl)-2-(4-cyclopentylpiperazine-1-yl)-ethyl]-urea

EXAMPLE 112

N-Phenyl-N'-[2-phenyl-2-4-cyclohexylpiperazine-1-yl-ethyl]-urea

EXAMPLE 113

N-2-Chlorophenyl-N'-[2-phenyl-2-(4-cyclohexylpiperazine-1-yl)-ethyl]-urea

EXAMPLE 114

N-2-Methoxyphenyl-N'-[2-phenyl-2-(4-cyclohexylpiperazine-1-yl)-ethyl]-urea

EXAMPLE 115

N-3,5-Bistrifluoromethylphenyl-N'-[2-phenyl-2-(4-cyclohexylpiperazine-1-yl)-ethyl]-urea

EXAMPLE 116

N-3,5-Bistrifluoromethylphenyl-N'-[2-(2-methoxyphenyl)-2-(4-cyclohexylpiperazine-1-yl)-ethyl]-urea

EXAMPLE 117

N-3,5-Bistrifluoromethylphenyl-N'-[2-(3,4-dichlorophenyl)-2-(4-cyclohexylpiperazine-1-yl)-ethyl]-urea

EXAMPLE 118

N-3,5-Bistrifluormethylphenyl-N'-[3-phenyl-2-(4-cyclohexylpiperazine-1-yl)-prop-1-yl]-urea

EXAMPLE 119

N-3,5-Bistrifluoromethylphenyl-N'-[3,3-diphenyl-2-(4-cyclohexylpiperazine-1-yl))-prop-1-yl]-urea

EXAMPLE 120

N-3,5-Bistrifluoromethylphenyl-N'-[2-(2-methoxyphenyl)-2-(4-cycloheptylpiperazine-1-yl)-ethyl]-urea

EXAMPLE 121

N-3,5-Bistrifluoromethylphenyl-N'-[2-(2-methoxyphenyl)-2-(4-(2-cyclohexylethyl)piperazine-1-yl)-ethyl]-urea

EXAMPLE 122

N-Phenyl-N'-[2-phenyl-2-(4-Dhenylpiperazine-1-yl)-ethyl)-urea

EXAMPLE 123

N-3,5-Bistrifluoromethylphenyl-N'-2-phenyl-2-(4-phenylpiperazine-1-yl)-ethyl]-urea

EXAMPLE 124

N-3,5-Bistrifluoromethylphenyl-N'-[2-phenyl-2-(4-(2,6-dimethylphenyl)piperazine-1-yl)-ethyl]-urea

EXAMPLE 125

N-3,5-Bistrifluoromethylphenyl-N'-[2-phenyl-2-[4-(2-hydroxyrhenyl)piperazine-1-yl)-ethyl]-urea

EXAMPLE 126

N-3,5-Bistrifluoromethylphenyl-N'-[2-phenyl-2-(4-(2-methoxyphenyl)piperazine-1-yl-ethyl)-urea

EXAMPLE 127

N-3,5-Bistrifluoromethylphenyl-N'-[2-phenyl-2-(4-(3-methoxyphenyl)piperazine-1-yl)-ethyl]-urea

EXAMPLE 128

N-3,5-Bistrifluoromethylphenyl-N'-2-phenyl-2-(4-(4-methoxyphenyl)-piperazine-1-yl)-ethyl]-urea

EXAMPLE 129

N-3,5-Bistrifluoromethylphenyl-N'-[2-phenyl-2-(4-(2,4-dimethoxyphenyl)-piperazine-1-yl)-ethyl]-urea The bistrifluoromethylbenzyl-[2-phenyl-2-(4-(2,4-dimethoxyphenyl)piperazine-1-yl)-ethyl]amine is prepared as in Example 9. Further reaction is carried out analogously to Example 102.

EXAMPLE 130

N-3,5-Bistrifluoromethylphenyl-N'-[2-phenyl-2-(4-(3,5-dimethoxyphenyl)-piperazine-1-yl -ethyl]-urea

EXAMPLE 131

N-3,5-Bistrifluoromethylphenyl-N'-[2-phenyl-2-(4-2-methylthio)phenyl)piperazine-1-yl)-ethyl]-urea

EXAMPLE 132

N-3,5-Bistrifluoromethylphenyl-N'-[2-phenyl-2-(4-(2-fluorophenyl)-piperazine-1-yl)-ethyl]-urea

EXAMPLE 133

N-3,5-Bistrifluoromethylphenyl-N'-[2-phenyl-2-(4-(4-fluorophenyl)-piperazine-1-yl)-ethyl]-urea

EXAMPLE 134

N-3,5-Bistrifluoromethylphenyl-N'-[2-phenyl-2-(4-(4-trifluoromethylphenyl)-piperazine-1-yl)-ethyl]-urea

EXAMPLE 135

N-3,5-Bistrifluoromethylphenyl-N'-[2-phenyl-2-(4-(4-nitrophenyl)-piperazine-1-yl)-ethyl]-urea

EXAMPLE 136

N-3,5-Bistrifluoromethylphenyl-N'-[2-phenyl-2-(4-(4-chlorobenzyl)-piperazine-1-yl)-ethyl]-urea

EXAMPLE 137

N-3,5-Bistrifluoromethylphenyl-N'-[2-phenyl-2-(4-(3,4-methylenedioxybenzyllpiperazine-1-yl)-ethyl]-urea The 3,5-bistrifluoromethylbenzyl-[2-phenyl-2-(4-(3,4-methylenedioxybenzyl)-piperazine-1-yl)-ethyl]amine is prepared as in Example 9. Further reaction is carried out analogously to Example 102.

EXAMPLE 138

N-3,5-Bistrifluoromethylphenyl-N'-[2-phenyl-2-(4-(9-fluorenyl)piperazine-1-yl)-ethyl]-urea

EXAMPLE 139

N-Phenyl-N'-[2-2-methoxyphenyl)-2-(4-phenylpiperazine-1-yl)-ethyl]-urea

EXAMPLE 140

N-2-Chlorophenyl-N'-[2-2-methoxyphenyl-2-4-(phenylpiperazine-1-yl)-ethyl]-urea

EXAMPLE 141

N-2-Methoxyphenyl-N'-[2-2-methoxyphenyl)-2-(4-phenylpiperazine-1-yl)-ethyl]-urea

EXAMPLE 142

N-3,5-Bistrifluoromethylphenyl-N'-[2-(2-methoxyphenyl)-2-(4-phenylpiperazine-1-yl)-ethyl)]-urea

EXAMPLE 143

N-3,5-Bistrifluoromethylphenyl-N'-[2-(2-methoxyphenyl)-2-(4-2-methylphenyl)-piperazine-1-yl)-ethyl]-urea

EXAMPLE 144

N-3,5-Bistrifluoromethylphenyl-N'-[2-(2-methoxyphenyl-2-(4-(2,3-dimethylphenyl)piperazine-1-yl)-ethyl]-urea

EXAMPLE 145

N-3,5-Bistrifluoromethylphenyl-N'-[2-(2-methoxyphenyl)-2-(4-(2-chlorophenylipiperazine-1-yl)-ethyl]-urea

EXAMPLE 146

N-3,5-Bistrifluoromethylphenyl-N'-[2-phenyl-2-(4 benzyl)piperazine-1-yl)-ethyl]-urea

EXAMPLE 147

N-3,5-Bistrifluoromethylphenyl-N'-[2-(2-methoxyphenyl)-2-(4-benzylpiperazine-1-yl)-ethyl]-urea

EXAMPLE 148

N-3,5-Bistrifluoromethylphenyl-N'-[2-(2-methoxyphenyl)-2-(3,4-methylenedioxybenzyl-piperazine-1-yl)-ethyl]-urea

EXAMPLE 149

N-3,5-Bistrifluoromethylphenyl-N'-[2-phenyl-2-(4-(2-phenylethyl)-piperazine-1-yl)-ethyl]-urea

EXAMPLE 150

N-3,5-Bistrifluoromethyl-phenyl-N'-[2-(2-methoxyphenyl)-(4-2-phenylethyl)-piperazine-1-yl)-ethyl]-urea

EXAMPLE 151

N-3,5-Bistrifluoromethylphenyl-N'-[2-2-methoxyphenyl)-2-(4-(1-phenylethyl)-piperazine-1-yl)-ethyl]-urea

EXAMPLE 152

N-Phenyl-N'-[2-(2-methoxyphenyl)-2-(4-benzhydrylpiperazine-1-yl)-ethyl]-urea

EXAMPLE 153

N-3,5-Bistrifluoromethylphenyl-N'-[2-(2-methoxyphenyl-2-[4-2-indanyl)piperazine-1-yl-ethyl]-urea

EXAMPLE 154

N-3,5-Bistrifluoromethylphenyl-N'-[-2-(2-methoxyphenyl-2-(4-1,2,3,-tetrahydronaphth-2-yl)piperazine-1-yl-ethyl]-urea

EXAMPLE 155

N-3,5-Bistrifluoromethylphenyl-N'[-2-(2-methoxyphenyl)-2-(4-benzhydrylpiperazine-1-yl-ethyl]-urea

EXAMPLE 156

N-3,5-Bistrifluoromethylphenyl-N'-[2-(2-methoxyphenyl)-2-(4-(2-pyridyl)piperazine-1-yl-ethyl]-urea

EXAMPLE 157

N-3,5-Bistrifluoromethylphenyl-N'-[2-(2-methoxyphenyl)- 2-(4-(2-pyrimidyl)piperazine-1-yl-ethyl]-urea

EXAMPLE 158

N-3,5-Bistrifluoromethylphenyl-N'-[2-(2-methoxyphenyl)- 2-(4-(2-guinolinyl)piperazine-1-yl)-ethyl]-urea

EXAMPLE 159

N-3,5-Bistrifluoromethylphenyl-N'-[2-(2-methoxyphenyl)-2-(4-cyclohexylhomopiperazine-1-yl)-ethyl]-urea

EXAMPLE 160

N-Phenyl-N'-[2-(2-methoxyphenyl)-2-(pioeridin-1-yl)-ethyl]-urea

EXAMPLE 161

N-2,5-Dimethylphenyl-N'-[2-(2-methoxyphenyl-2-piperidin-1-yl)-ethyl]-urea

EXAMPLE 162

N-2-Methylphenyl-N'-[2-(2-methoxyphenyl)-2-(piperidin-1-yl)-ethyl]-urea

EXAMPLE 163

N-2-Chlorophenyl-N'-[2-(2-methoxyohenyl)-2-(piperidin-1-yl)-ethyl]-urea

EXAMPLE 164

N-3,4-Dichlorophenyl-N'-[2-(2-methoxyphenyl)-2-(piperidin-1-yl)-ethyl]-urea

EXAMPLE 165

N-2-Methoxyphenyl-N'-[2-(2-methoxyphenyl)-2-(piperidin-1-yl)-ethyl]-urea

EXAMPLE 166

N-3,5-Bistrifluoromethylphenyl-N'-[2-(2-methoxyphenyl)-2-piperidin-1-yl)-ethyl]-urea

EXAMPLE 167

N-3,5-Bistrifluoromethylphenyl-N'-[2-phenyl-2-(piperidin-1-yl-ethyl]-urea

EXAMPLE 168

N-3,5-Bistrifluoromethylphenyl-N'-[2-(2-methoxyphenyl)-2-(2-methylpiperidin-1-yl-ethyl]-urea

EXAMPLE 169

N-3,5-Bistrifluoromethylphenyl-N'-[2-(2-methoxyphenyl)-2-(3-methylpiperidin-1-yl-ethyl]-urea

EXAMPLE 170

N-3,5-Bistrifluoromethylphenyl-N'-[2-(2-methoxyphenyl)-2-(4-methylpiperidin-1-yl-ethyl]-urea

EXAMPLE 171

N-3,5-Bistrifluoromethylphenyl-N'-[2-(2-methoxyphenyly-2-(4-cyclohexylpiperidin-1-yl)-ethyl]-urea

EXAMPLE 172

N-3,5-Bistrifluoromethylphenyl-N'-[2-(2-methoxyphenyl)-2-5,dimethylpiperidin-1-yl)-ethyl]-urea

EXAMPLE 173

N-3,5-Bistrifluoromethylphenyl-N'-[2-(2-methoxyphenyl)-2-(3-phenylpiperidin-1-yl)-ethyl]-urea

EXAMPLE 174

N-3,5-Bistrifluoromethylphenyl-N'-[2-(2-methoxyphenyl)-2-(4-phenylpiperidin-1-yl)-ethyl]-urea

EXAMPLE 175

N-3,5-Bistrifluoromethylphenyl-N'-[2-(2-methoxyphenyl)-2-(4-benzylpiperidin-1-yl)-ethyl]-urea

EXAMPLE 176

N-3,5-Bistrifluoromethylphenyl-N'-[2-(2-methoxyphenyl)-2-(nortropan-8-yl)-ethyl]-urea

EXAMPLE 177

N-3,5-Bistrifluoromethylphenyl-N'-[2-(2-methoxyphenyl)-2-(4-piperidin-1-yl-piperidin-1-yl-ethyl]-urea

EXAMPLE 178

N-3,5-Bistrifluoromethylphenyl-N'-[2-4-dichlorophenyl)-2-(4-piperidin-1-yl)-piperidin-1-yl-ethyl]-urea

EXAMPLE 179

N-3,5-Bistrifluoromethylphenyl-N'-[2-(2-methoxyphenyl-2-(4-(2-isoindolinyl)-piperidin-1-yl)-ethyl]-urea

EXAMPLE 180

N-3,5-Bistrifluoromethylphenyl-N'-[2-(2-methoxyphenyl)-2-(4-(1,2,3,4-tetrahydroisoguinolin-2-yl)-piperidin-1-yl-ethyl]-urea The following Examples may also be prepared analogously to the processes described hereinafter:

EXAMPLE 181

N-3,5-Bistrifluoromethylphenyl-N'-[2-phenyl-2-(4-(2-(4-chlorophenyl)ethyl)piperazine-1-yl)ethyl]-urea

EXAMPLE 182

3,5-Bistrifluoromethylbenzyl-[2-phenyl-2-(4-(2-(4-chlorophenyl)ethyl)piperazine-1-yl)ethyl]-amine

EXAMPLE 183

N-3,5-Bistrifluoromethylphenyl-N'-[2-phenyl-2-(4-(2-(4-methoxyphenyl)ethyl)piperazine-1-yl)ethyl]-urea

EXAMPLE 184

3,5-Bistrifluoromethylbenzyl-[2-phenyl-2-(4-(2-(4-methoxyphenyl)ethyl)piperazine-1-yl)ethyl]-amine

EXAMPLE 185

N-[ 2-Phenyl-2-(4-(2-cyclopropylethyl)piperazine-1-yl)ethyl]-2-(3,5-bistrifluoromethyl-phenyl)-acetamide

EXAMPLE 186

N-[2-Phenyl-2-(4-(2-phenylpropyl)piperazine-1-yl)ethyl]-2-(3,5-bistrifluoromethyl-phenyl)-acetamide

EXAMPLE 187

N-[2-Phenyl-2-(4-ethylpiperazine-1-yl)ethyl]-2-(3,5-bistrifluoromethylphenyl)-acetamide

EXAMPLE 188

N-[2-Thien-3-yl-2-(4-cyclohexylpiperazine-1-yl)ethyl]-2-(3,5-bistrifluoromethylphenyl)-acetamide

EXAMPLE 189

N-(2-Thien-2-yl-2-(4-cyclohexylpiperazine-1-yl)ethyl-2-(3,5-bistrifluoromethylphenyl)-acetamide

EXAMPLE 190

N-[2-Phenyl-2-(4-(2-(3,4-dichlorophenyl ethyl)piperazine-1-yl)ethyl]-2-(3,5-bistrifluoro-methylphenyl)-acetamide

EXAMPLE 191

3,5-Bistrifluoromethylbenzyl-[2-(2-methoxyphenyl)-2-(3-hydroxymethylpiperidine-1-yl)-ethyl]-amine

EXAMPLE 192

3,5-Bistrifluoromethylbenzyl-[2-(2-methoxyphenyl)-2-( 4-(2-hydroxyethyl)piperidine-1-yl)-ethyl]-amine

EXAMPLE 193

3,5-Bistrifluoromethylbenzyl-[2-(1-naphthyl)-2-(4-cyclohexylpiperidine-1-yl)-ethyl]-amine

EXAMPLE 194

N-2-(2-Methoxyphenyl)-2-(4-(piperidine-1-yl)piperidine-1-yl)-ethyl)-2-(3-(2-propyloxy)phenyl)acetamide

EXAMPLE 195

N-3,5-Bistrifluoromethylphenyl-N'-[2-(2-methoxyphenyl)- 2-(4-propylpiperidine-1-yl)-ethyl]-urea

EXAMPLE 196

N-[2-(3,4-Dichlorophenyl-2-(4-(piperidine-1-yl)piperidine-1-yl)-ethyl]-2-(3-(2-propyloxyy)phenyl)acetamide

EXAMPLE 197

1-(3,5-Bistrifluoromethylphenyl)-2'-(2-methoxyphenyl)-2'-(4-cyclohexylpiperazine-1-yl)-diethylamine

EXAMPLE 198

N-[2-(3,4-Dichlorophenyl)-2-(4-cyclohexylpiperazine-1-yl)-ethyl]-2-(3,5-bistrifluoro-methylphenyl)acetamide

EXAMPLE 199

N-[2-[2-Methoxyphenyl)-2-(4-cyclohexylpiperazine-1-yl)-ethyl]-2-(3-(2-propyloxy)phenyl)acetamide

EXAMPLE 200

N-3,5-Bistrifluoromethylphenyl-N'-12-(2,6-dichlorophenyl)-2-(4-cyclohexylpiperazine-1-yl)ethyl]-urea

EXAMPLE 201

N-[2-(2,6-Dichlorophenyl)-2-(4-cyclohexylpiperazine-1-yl)-ethyl]-2-(3,5-bistrifluormethylphenyl)acetamide

EXAMPLE 202

3,5-Bistrifluoromethylbenzyl-[2-(2,6-dichlorophenyl)-2-(4-cyclohexylpiperazine-1-yl)-ethyl]-amine

EXAMPLE 203

N-3,5-Bistrifluoromethylphenyl-N'-[2-(2,3-dichlotophenyl)-2-(4-cyclohexylpiperazine-1-yl)ethyl]-urea

EXAMPLE 204

3,5-Bistrifluoromethylbenzyl-[2-(2,3-dichlorophenyl)-2-(4-cyclohexylpiperazine-1-yl)-ethyl]-amine

EXAMPLE 205

N-[2-(2,3-Dichlorophenyl)-2-(4-cyclohexylpiperazine-1-yl)-ethyl]-2-(3,5-bistrifluormethylphenyl)acetamide

EXAMPLE 206
1-(3,5-Bistrifluoromethylphenyl)-2'-(3,4-dichlorophenyl)-2'-(4-(piperidine-1-yl)piperidine-1-yl)-diethylamine

EXAMPLE 207
1-(3,5-Bistrifluoromethylphenyl)-2'-(3,4-dichlorophenyl)-2-(4-(piperidine-1-yl)piperidine-1-yl)-diethylamine Diastereomers of Example 211

EXAMPLE 208
N-3,5-Bistrifluoromethylphenyl-N'-2-(1-naphthyl)-2-(4-cyclohexylpiperazine-1-yl)ethyl]-urea

EXAMPLE 209
N-[2-(1-Naphthyl)-2-(4-cyclohexylpiperazine-1-yl)-ethyl]-2-(3,5-bistrifluoromethylphenyl)acetamide

EXAMPLE 210
1-(3,5-Bistrifluoromethylphenyl)-2'-(2,3-dichlorophenyl)-2'-(4-cyclohexylpiperazine-1-yl)-diethylamine

EXAMPLE 211
1-(3,5-Bistrifluoromethylphenyl)-2'-(2,3-dichlorophenyl)-2'-(4-cyclohexylpiperazine-1-yl)-diethylamine Diastereomers of Example 215

EXAMPLE 212
1-(3,5-Bistrifluoromethylphenyl-2'-2-(2,6-dichlorophenyl)-2'-(4-cyclohexylpiperazine-1-yl)-diethylamine

EXAMPLE 213
N-[2-(3,4-Dichlorophenyl)-2-(4-(piperidine-1-yl)piperidine-1-yl)-ethyl]-2-(3,5-dimethyl-phenyl)acetamide

EXAMPLE 214
N-[2-(2-Methoxyphenyl)-2-(4-(piperidine-1-yl)piperidine-1-yl)-ethyl]-2-(3,5-dimethylphenyl)acetamide

EXAMPLE 215
N-[2-(2-Methoxyphenyl)-2-(4-cyclohexylpiperazine-1-yl)-ethyl]-2-(3,5-dimethylphenyl)acetamide

EXAMPLE 216
3,5-Bistrifluoromethylbenzyl-[2-(2,6-dichlorophenyl)-2-(4-(piperidine-1-yl)piperidine-1-yl)-ethy]-amine

EXAMPLE 217
N-3,5-Bistrifluoromethylphenyl-N'-[2-(2,6-dichlorophenyl)-2-(4-(piperidine-1-yl)piperidine-1-yl)ethyl]-urea

EXAMPLE 218
N-[2-(2,6-Dichlorophenyl)-2-(4-(piperidine-1-yl)piperidine-1-yl)-ethyl]1-2-(3,5-bistrifluoromethylphenyl)acetamide

EXAMPLE 219
N-[2-(3,4-Dichlorophenyl)-2-(4-cyclohexylpiperazine-1-yl)-ethyl]-2-(3,5-dimethylphenyl)acetamide

EXAMPLE 220
N-[2-(2,6-Difluorophenyl)-2-(4-cyclohexylpiperazine-1-yl)-ethyl]-2-(3,5-bistrifluormethylphenyl)acetamide

EXAMPLE 221
1-(3,5-Bistrifluoromethylphenyl)-2-(2,3-dichlorophenyl-2-(4-(piperidine-1-yl)piperidine-1-yl)-diethylamine

EXAMPLE 222
N-[2-(2,3-Dichlorophenyl)-2-(4-(piperidine-1-yl)piperidine-1-yl)-ethyl]-2-(3,5-bistrifluorimethylphenyl)acetamide

EXAMPLE 223
1-(3,5-Bistrifluoromethylphenyl)-2'-(2,6-dichlorophenyl)-21-(4-(piperidine-1-yl)piperidine-1-yl)-diethylamine

EXAMPLE 224
N-[2-(2-Fluorophenyl)-2-(4-cyclohexylpiperazine-1-yl)-ethyl]-2-(3,5-bistrifluormethylphenyl)acetamide

EXAMPLE 225
N-[2-(3-Fluorophenyl)-2-(4-cyclohexylpiperazine-1-yl)-ethyl]-2-(3,5-bistrifluoromethylphenyl)acetamide

EXAMPLE 226
3,5-Bistrifluoromethylbenzyl-[2-(2,3-dichlorophenyl)-2-(4-(piperidine-1-yl)piperidine-1-yl)-ethyl]-amine

EXAMPLE 227
N-[2-(3,4-Dichlorophenyl)-2-(4-(piperidine-1-yl)piperidine-1-yl)-ethyl]-3,5-bistrifluoromethylbenzamide

EXAMPLE 228
N-[2-(2,3-Difluorophenyl)-2-(4-cyclohexylpiperazine-1-yl)-ethyl]-2-(3,5-bistrifluormethylphenyl)acetamide

EXAMPLE 229
N-[2-(3,5-Difluorophenyl)-2-(4-cyclohexylpiperazine-1-yl)-ethyl]-2-(3,5-bistrifluoromethylphenyl)acetamide

EXAMPLE 230
N-[2-(2-Fluorophenyl)-2-(4-(piperidine-1-yl)piperidine-1-yl)-ethyl]-2-(3,5-bistrifluoromethylphenyl)acetamide

EXAMPLE 231
N-[2-(3-Fluorophenyl)-2-(4-(piperidine-1-yl)piperidine-1-yl)-ethyl]-2-(3,5-bistrifluoromethylphenyl)acetamide

EXAMPLE 232
N-[2-(4-Fluorophenyl)-2-(4-(piperidine-1-yl)piperidine-1-yl)-ethyl]-2-(3,5-bistrifluoromethylphenyl)acetamide

EXAMPLE 233
N-[2-(2,3-Difluorophenyl)-2-(4-(piperidine1-yl)piperidine-1-yl)-ethyl]-2-(3,5-bistrifluoromethylphenyl)acetamide

EXAMPLE 234
N-[2-(3,4-Difluorophenyl)-2-(4-(piperidine-1-yl)piperidine-1-yl)-ethyl]-2-(3,5-bistrifluoromethylphenyl)acetamide

EXAMPLE 235
2-(3,5-Bistrifluoromethylphenyl)-2'-(3,4-dichlorophenyl)-2'-(4-(piperidine-1-yl)piperidine-1-yl)-diethylamine

EXAMPLE 236
N-[2-(2,4-Difluorophenyl)-2-(4-(piperidine-1-yl)piperidine-1-yl)-ethyl]-2-(3,5-bistrifluoromethylphenyl)acetamide

EXAMPLE 237
N-[2-(3,4-Dichlorophenyl)-2-(4-(piperidine-1-yl)piperidine-1-yl)-ethyl]-N-methyl-3,5-bistrifluoromethylbenzamide

EXAMPLE 238
N-[2-(3,4-Dichlorophenyl)-2-(4-(piperidine-1-yl)piperidine-1-yl)-ethyl]-N-methyl-2-(3,5-bistrifluoromethylphenyl)acetamide

EXAMPLE 239

N-[2-Phenyl-2-(4-cyclohexylpiperazine-1-yl)-ethyl]-2-(3,5-bistrifluoromethylphenyl)-acetamide

EXAMPLE 240

N-[2-(2,3-Methylendioxyphenyl)-2-(4-(piperidine-1-yl)piperidine-1-yl)-ethyl]-2-(3,5-bistrifluormethylphenyl)acetamide

EXAMPLE 241

2-(3,5-Bistrifluoromethylphenyl)-2'-phenyl-2'-(4-cyclohexylpiperazine-1-yl)-diethylamine

EXAMPLE 242

N-[2-(3,4-Methylendioxyphenyl)-2-(4-(piperidine-1-yl)piperidine-1-yl)-ethyl]-2-(3,5-bistrifluormethylphenyl)acetamide

EXAMPLE 243

2-(3,5-Bistrifluoromethylphenyl)-2'-(2,3-methylendioxyphenyl)-2'-(4-(piperidine-1-yl)piperidine-1-yl)-diethylamine

EXAMPLE 244

2-(3,5-Bistrifluoromethylphenyl)1-2'-(3,4-methylendioxyphenyl)-2'-(4-(piperidine-1-yl)piperidine-1-yl)-diethylamine

EXAMPLE 245

N-3,5-Bistrifluoromethylbenzyl-N-[2-2,3-dichlorophenyl)-2-(4-(piperidine-1-yl)piperidine-1-yl)-ethyl]acetamide

EXAMPLE 246

2-(3,5-Bistrifluoromethylphenyl)-2'-(3,4-dichlorophenyl)-21-4-(piperidine-1-yl)piperidine-1-yl)diethylmethylamine

EXAMPLE 247

N-[2-(3,4-Dichlorophenyl)-2-(4-(morpholine-4-yl)piperidine-1-yl)-ethyl]-2-(3,5-bistrifluoromethylphenyl)acetamide

Pharmaceutical Preparations

Injectable solution 200 mg Active substance*

1.2 mg Monopotassium dihydrogen phosphate=$KH_2PO_4$**

0.2 mg Di-sodium hydrogen phosphate=$NaH_2PO_4 \cdot 2H_2O$**

(** together constitute a buffer)

94 mg Sodium chloride# or mg Glucose#

(# sotonic)

4 mg Albumin (protease protection)

q.s. Sodium hydroxide solution++ q.s. Hydrochloric acid++

(++ to adjust the pH to pH 6)

Suficient water to make a 10 ml solution for injections

Injectable Solution 200 mg Active substance*

94 mg Sodium chloroide 520 mg Glucose 4 mg Albumin q.s. Sodium hydroxide solution++ q.s. Hydrochloric acid++

(++ adjust the pH to pH 9)

Suficient water to make a 10 ml solution for injections

Lyophilisate 200 mg Active substance*

520 mg Mannitol (isotonic substance/structural component)

4 mg Albumin

Solent 1 for lyophilisate 10 of water for injections

Solvent 2 for lyophilisate 20 mg of polysorbate®80=Tween®80 (surfactant)

10 of water for injections

* Active substance: Compounds according to the invention, eg. those of Examples 1 to 180.

Dosage for person weighing 67 kg: 1 to 500 mg.

We claim:

1. A compound of the formula I

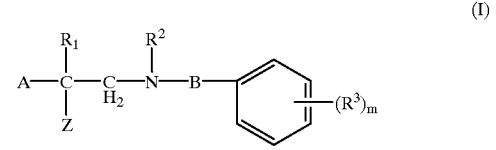

(I)

or a pharmaceutically acceptable salt thereof, wherein

A is Ar, Ar—CH(Ph)—, Ar—$(CH_2)_2$—, Ar—CH(Ph)—$CH_2$—, Ar—$CH_2$—CH(Ph)—, or Ar—CH(Ph)—CH(Ph)—, wherein Ar is phenyl optionally substituted by one to three $R^4$ groups, naphthyl, pyridyl, or thienyl; and Ph is phenyl optionally substituted by one to three $R^4$ groups;

$R^4$ is independently $(C_{1-6})$alkyl, $(C_{1-6})$alkyl substituted by 1 to 3 fluorine atoms, $(C_{1-6})$alkoxy, $(C_{1-6})$alkylthio or halogen; or two adjacent $R^4$ groups together are —O—$(CH_2)$—O— or —$(CH_2)_{3-5}$—;

B is —$CH(R^{12})$—, —$CH_2$—$CH_2$—, —C(O)—, —C(O)—NH—, —C(O)—$CH_2$— or —C(O)—$CH_2$—$CH_2$—;

wherein $R^2$ is H or $CH_3$;

$R^1$ is H, $(C_{1-6})$alkyl, or phenyl;

$R^2$ is H, $(C_{1-6})$alkyl, or —C(O)$(C_{1-3})$alkyl, wherein the alkyl groups contained therein may be substituted by a phenyl group;

$R^3$ is hydrogen, $(C_{1-6})$alkyl, $(C_{1-6})$alkyl substituted by 1 to 3 fluorine atoms, halogen or $(C_{1-6})$alkoxy;

m is 1, 2, or 3;

Z is

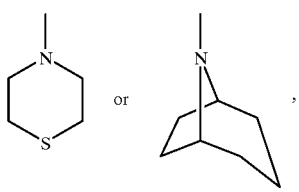

wherein
R⁹ is hydrogen, $(C_{3-7})$cycloalkyl, phenyl,

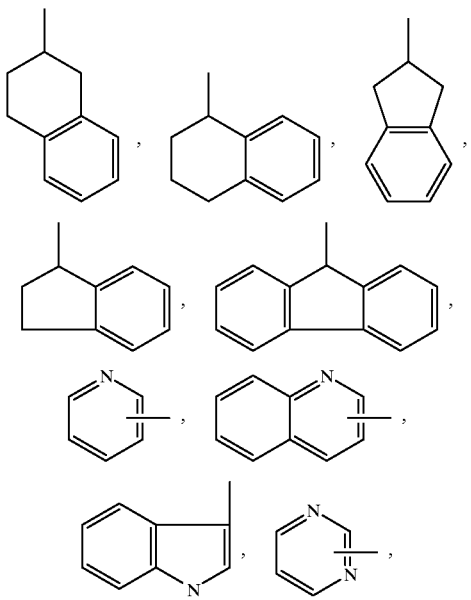

$(C_{1-6})$alkyl, allyl, —$(CH_2)_{2-6}OH$, —$(C_{1-3})$ alkylphenyl, diphenylmethyl radical, or —$(C_{1-3})$ alkyl$(C_{3-7})$cycloalkyl, wherein the phenyl groups contained in the above-mentioned groups are unsubstituted or substituted by one or two substituents selected from $CH_3$, F, Cl, $OCH_3$, $SCH_3$, $CF_3$, OH, or $NO_2$, or they are substituted by —O—$CH_2$—O— linked to 2 adjacent carbon atoms of the phenyl;
or R⁹ is —$CH_2OH$, —OH,

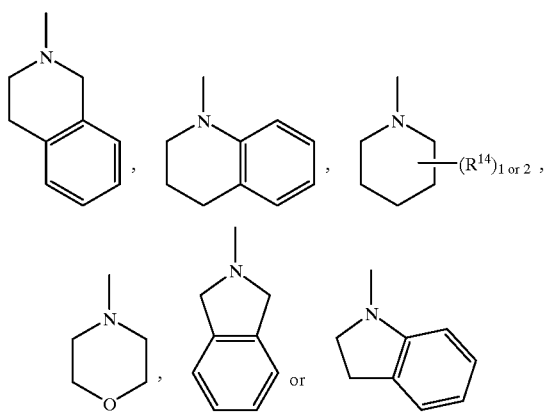

wherein the last six groups mentioned are in position 3, and wherein $R^{14}$ is H, $(C_{1-6})$ alkyl, phenyl, or cyclohexyl,
wherein if one of the $R^{14}$ groups is phenyl or cyclohexyl, the other $R^{14}$ must be hydrogen; with the proviso that when:
B is —$CH_2$—, $R^1$ is H, alkyl, or phenyl, $R^2$ is H, then Z is not

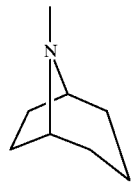

2. A compound according to claim 1, wherein
A is Ar, Ar—CH(Ph)—, Ar—$(CH_2)_2$—, Ar—CH(Ph)—$CH_2$—, Ar—$CH_2$—CH(Ph)— or Ar—CH(Ph)—CH(Ph)—, wherein Ar is phenyl optionally substituted by one to three $R^4$ groups, or naphthyl; and
Ph is phenyl optionally substituted by one to three $R^4$ groups;
$R^4$ is independently $(C_{1-3})$alkyl, $(C_{1-3})$alkyl substituted by 1 to 3 fluorine atoms, $(C_{1-3})$alkoxy, $(C_{1-3})$alkylthio or halogen; or two adjacent $R^4$ groups together are —O—$(CH_2)$—O—;
B is —CH($R^{12}$)—, —$CH_2$—$CH_2$—, —C(O)—, —C(O—NH—, —C(O)—$CH_2$— or —C(O)—$CH_2$—$CH_2$—;
wherein
$R^{12}$ is H or $CH_3$;
$R^1$ is H, $(C_{1-3})$alkyl, or phenyl;
$R^2$ is H, $(C_{1-3})$alkyl, or —C(O)$(C_{1-3})$alkyl, wherein the alkyl groups contained therein may be substituted by a phenyl group;
$R^3$ is hydrogen, $(C_{1-3})$alkyl, $(C_{1-3})$alkyl substituted by 1 to 3 fluorine atoms, halogen or $(C_{1-3})$alkoxy;
m is 1, 2, or 3.

3. A compound according to claim 1 or 2, wherein A is phenyl, benzyl, diphenylmethyl radical or naphthyl.

4. A compound according to claim 3, wherein A is unsubstituted phenyl or phenyl substituted by 1 or 2 $R^4$ groups, these $R^4$ groups independently of each other representing methyl, trifluoromethyl, methoxy, methylthio, fluorine or chlorine.

5. A compound according to claim 4, wherein A is phenyl or methoxyphenyl.

6. A compound according to claim 1, wherein:
B is —$CH_2$—,
—$CH(CH_3)$—,
—$CH_2$—$CH_2$—,
—C(O)—,
—C(O)—NH— or
—C(O)—$CH_2$—.

7. A compound according to claim 1, wherein $R^1$ is hydrogen.

8. A compound according to claim 1, wherein $R^2$ is —C(O)$CH_3$.

9. A compound according to claim 1, wherein $R^2$ is hydrogen.

10. A compound according to claim 1, wherein $R^3$ is hydrogen, methyl, trifluoromethyl, methoxy, i-propoxy, fluorine or chlorine.

11. A compound according to claim 1, wherein m is 1 or 2.

12. A compound according to claim 1, wherein m is 1 and $R^3$ is i-propoxy in position 3.

13. A compound according to claim 1, wherein Z represents

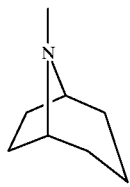

14. A pharmaceutic preparation comprising a compound according to claim 1 and one or more solubilizers, emulsifiers or adjuvants.

15. A method for treating neurokinin-mediated diseases selected from the group consisting of asthma, bronchitis, rhinitis, coughs, expectoration, conjunctivitis, dermatitis, urticaria, ulcerative colitis, Crohn's disease, polyarthritis, osteoarthritis, migraine, vascular headaches, and vomiting which method comprises administering to a host in need of such treatment a therapeutically effective amount of a compound according claim 7.

16. A compound according to claim 13 which is N-3,5-Bistrifluoromethylphenyl-N'-[2-(2-methoxyphenyl)-2-(nortropan-8-yl)-ethyl]-urea.

17. A process of making a compound of the formula I according to claim 1, comprising:

forming a compound wherein $R^2$ is H:

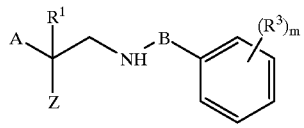

(I)

comprising reacting a compound of the formula (IV):

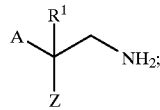

(IV)

with a) an isocyanate compound:

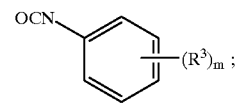

to form compounds of the formula I wherein B is —C(O)—NH— and wherein $R^9$ is not OH;

b) carboxylic acid of the formula:

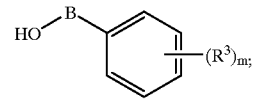

to form compounds of the formula I wherein the B is a group —C(O)—, —C(O)—CH$_2$—or —C(O)—CH$_2$—CH$_2$—, and $R^2$ is H;

c)

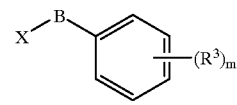

wherein X is a leaving group selected from the group consisting of; chlorine, bromine, O-tosylate and O-triflate;

to form compound of the formula I wherein B is a group —CH($R^2$)— or —CH$_2$—CH$_2$—; OR d) a carbonyl compound:

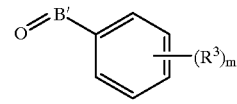

wherein B' is =C($R^2$)— or =CH—CH$_2$— and $R^9$ is not NO$_2$, to obtain an imine which is subsequently reduced or both components are subjected to an reductive amination;

and in order to prepare compounds of the formula I wherein $R^2$ is ($C_1$-$C_6$)alkyl or —C(O)—($C_1$-$C_3$) alkyl, the compound of the formula I wherein $R^2$ is H is further reacted with a reagant containing the desired group $R^2$ and the resulting compound is isolated in the free form or in the form of the desired salt.

* * * * *

UNITED STATES PATENT AND TRADEMARK OFFICE
CERTIFICATE OF CORRECTION

PATENT NO. : 6,235,732 B1
DATED : May 22, 2001
INVENTOR(S) : H. Dollinger et al.

It is certified that error appears in the above-identified patent and that said Letters Patent is hereby corrected as shown below:

Column 7,
Line 25, "—(C1-$C_2$)alkylphenyl" should read -- —($C_1$-$C_2$)alkylphenyl --.

Column 35,
Line 60, "sotonic" should read -- isotonic --;
Line 66, "Suficient" should read -- Sufficient --.

Column 36,
Line 10, "Suficient" should read -- Sufficient --;
Line 19, "Solent" should read -- Solvent --;
Line 24, after "10" insert -- ml --.

Column 36, claim 1,
Line 59, "$R^2$" should read -- $R^{12}$ --.

Column 39, claim 14,
Line 15, "pharmaceutic" should read -- pharmaceutical --.

Signed and Sealed this

Sixth Day of November, 2001

Attest:

NICHOLAS P. GODICI
*Attesting Officer*  *Acting Director of the United States Patent and Trademark Office*